United States Patent [19]

Gargiulo et al.

[11] 4,167,449

[45] Sep. 11, 1979

[54] COMPOSITION AND METHOD FOR DETERMINING TRANSFERASE AND PROTEASE ACTIVITY

[75] Inventors: Robert J. Gargiulo, Miami, Fla.; Richard C. Driscoll, Lake Forest, Ill.

[73] Assignee: American Hospital Supply Corporation, Evanston, Ill.

[21] Appl. No.: 822,057

[22] Filed: Aug. 5, 1977

Related U.S. Application Data

[63] Continuation-in-part of Ser. No. 709,720, Jul. 29, 1976, abandoned.

[51] Int. Cl.$^2$ .................... G01N 31/14; G01N 33/16
[52] U.S. Cl. .......................... 435/16; 435/24
[58] Field of Search .................. 260/112.5 R, 112 R, 260/518 R, 554 R, 534 G; 23/230 B; 195/103.5 R, 99

[56] References Cited

U.S. PATENT DOCUMENTS

| 3,591,459 | 7/1971 | Haschen et al. | 195/103.5 R |
|---|---|---|---|
| 3,773,626 | 11/1973 | Bernt et al. | 195/103.5 R |
| 3,862,011 | 1/1975 | Smith | 195/103.5 R |
| 3,878,048 | 4/1975 | Carroll | 195/99 |
| 3,892,631 | 7/1975 | Carroll | 195/99 |
| 3,979,447 | 9/1976 | Bernt et al. | 195/103.5 R |
| 4,070,245 | 1/1978 | Svendsen | 195/99 |

OTHER PUBLICATIONS

Wildes et al, "Differences Between Excited States Produced Chemically and Photochemically. Ion Pairs of Excited States Derived From Luminol", J. Amer. Chem. Soc., vol. 95, No. 8, (1973) pp. 2610–2617.
Bayley et al, "Coformational Properties of Pig-heart Cytoplasmic Aspartate Aminotransferase. Circular-Dichromism and Absorption-Steptroscopy Study of Dicarboxylic Binding", Chem. Abstracts. vol. 83, No. 15, p. 223, (1975) Abs. No. 128,197a.

Primary Examiner—Thomas G. Wiseman
Attorney, Agent, or Firm—Tilton, Fallon, Lungmus & Chestnut

[57] ABSTRACT

Transferase and protease activity in homogenates and biological solutions is fluorometrically determined at wavelengths corresponding generally to those used for fluorometric NADH-linked determinations by utilizing novel substrate compositions consisting essentially of certain fluorogenic 5-aminoisophthalic acid derivatives coupled to amino acid constituents specific to the transferases and proteases under investigation.

14 Claims, No Drawings

COMPOSITION AND METHOD FOR DETERMINING TRANSFERASE AND PROTEASE ACTIVITY

RELATED APPLICATION

This application is a continuation-in-part of co-pending application Ser. No. 709,720, filed July 29, 1976, now abandoned.

BACKGROUND

Enzyme substrates with naphthylamines as chromogenic groups linked to other amino acids have been described in the literature for the determination of transferases and proteases, such as γ-glutamyl transpeptidase, lecuine aminopeptidase, oxytocinase, and trypsin. Orlowski et al, Clin. Chim, Acta, 7:755–760 (1962), and references cited therein. The determination of transferase and protease activity in human serum, urine, and tissues may have diagnostic significance; for example, the assay of γ-glutamyl transpeptidase activity in human serum may be useful in the differential diagnosis of liver diseases, because the enzyme activity is particularly high in obstructive jaundice and liver cancer while lower activities are observed in viral hepatitis and liver cirrhosis. Orlowski et al, supra. See also Rosalki et al, Ann. Clin. Biochem. 7:143 (1970). The majority of studies with respect to γ-glutamyl transpeptidase determinations have been carried out using naphthylamines in formulating the substrates and, unfortunately, the products (i.e., naphthylamines) are both toxic and carcinogenic, presenting undesirable risks for general laboratory use.

Many of the enzyme assays commonly performed in clinical laboratories are NADH linked; that is, they involve a series of reactions which ultimately result in the reduction of nicotinamide adenine dinucleotide (NAD) to its reduced form, NADH. The NADH is then detected spectrophotometrically or fluorometrically. The more recent fluorometric procedures have the characteristic advantages of simplicity, speed, and economy, and often have the further advantage of greater sensitivity. Typically, a fluorometric NADH-linked test involves the use of a filter fluorometer which directs ultraviolet light at a wavelength of about 340 nm against the surface of the sample and which measures the fluorescence, or rate of change of fluorescence at an emission wavelength of about 465 nm.

Other references illustrating the state of the prior art are U.S. Pat. Nos. 3,979,447, 3,862,011, 3,773,626, 3,591,458, 3,878,048, 3,892,631, and Wildes et al, J. Am. Chem. Soc., 95:8, 2610 (1973), and Bayley et al, Eur. J. Biochem. 56 (2), 455–65 (1975).

SUMMARY

This invention involves the discovery of certain compositions of matter useful as enzyme substrates in the fluorometric determination of transferase (or transpeptidase) activity in homogenates and biological fluids. Such substrates are believed novel and are relatively safe for laboratory use. An especially important advantage is that such substrates yield, upon cleavage by the enzymes under investigation, fluorogenic moieties which have peak fluorometric excitation and emission values approximately those of NADH-linked tests and, therefore, assays for fluorometrically determining transferase or protease activity by the use of such substrates may be conducted with standard fluorometers using the same filters intended for conventional NADH-linked assays. Thus, a transferase such as γ-glutamyl transpeptidase may be measured using the same fluorometric equipment and filters used for conducting assays of other enzymes such as SGOT, SGPT, CPK, LDH, and HBD.

DESCRIPTION

The enzyme substrates involved in this invention are 5-aminoisophthalic acid derivatives of the general formula

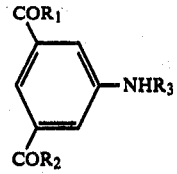

and wherein each of $R_1$ and $R_2$ is —OH, —NH$_2$, —NHCH$_3$, —NHC$_2$H$_5$, —N(CH$_3$)$_2$, —N(C$_2$H$_5$)$_2$, —N(CH$_3$)(C$_2$H$_5$), —OCH$_3$, or —O(CH$_2$)$_n$CH$_3$, n is an integer from 1 through 4, and wherein $R_3$ is an amino acid moiety capable of being cleaved from the remainder of the substrate when exposed to a transferase or protease having activity specific to that substrate, in some cases in the presence of glycylglycine or some other appropriate acceptor such as glutamate, glycine, or glycylglycylglycine. Such substrates which have amino acid moieties (that may comprise several amino acid groups) and which are specific to various transferases and proteases are as follows:

| Substrate | Enzyme |
|---|---|
| (A)-lys-ala | DAP-II |
| (A)-Z-ala-arg-arg | Catheps in B 1 |
| (A)-BZ-val-lys-lys-arg | Cathepsin B 1a |
| (A 2-HCl)CBZ-arg-arg | Cathepsin B 1 |
| (A-diacetate)-N-CBZ-arg-arg-arg | Trypsin |
| (A 3-HCl)-L-arg-arg | DAP III |
| (A)-Z-gly-gly-arg | Anionic Trypsin, Plasminogen Activator, Proinsulin Converting Enzyme |
| (A)-pro-arg | DAP-I or Cathepsin C |
| (A)-α-BZ-phe-val-arg | Thrombin |
| (di-A)-L-cystine | Oxytocinase |
| (A)-γ-glutamyl | γ-Glutamyl Transpeptidase |
| (A formate)-L-leu-gly-gly | |
| (A)-leu | Aminopeptidase |
| (A)-BZ-arg-pro-gly-phe-phe-leu | Cathepsin D |
| (A)-phe-pro-ala-met | Cathepsin B 1b |
| (A)-glutaryl-gly-L-phe | |

| Substrate | Enzyme |
|---|---|
| (A)-gly-pro | DAP-IV |
| (A)-CBZ-pro-ala-gly-pro | Collagenase |
| (A)-his-ser | DAP I or Cathepsin C |
| (A)-N-CBZ-L-pro-L-phe-L-his-L-leu-L-leu-L-val-L-tyr-L-ser | |
| (A)-N-CBZ-gly-L-met | Renin |
| (A)-glutaryl-ala-ala | Elastase |
| (A)-BZ-arg-pro-gly-phe-phe-pro | Cathepsin D |
| (A)-ala | Aminopeptidase B |
| (A)-BZ-arg | Trypsin/Cathepsin B 1 |
| (A)-BZ-arg-gly-leu | |
| (A)-met | |
| (A)-BZ-arg-gly-tyr | DAP-I |
| (A)-ser-tyr | Cathepsin C |

In the above, the designations constitute established abbreviations as follows: ala (alanine), arg (arginine), BZ (benzoyl), CBZ and Z (carbobenzoxy), gly (glycine), his (histidine), leu (leucine), lys (lysine), met (methionine), phen (phenylalanine), pro (proline), ser (serine), tyr (tyrosine), val (valine). To increase solubility rates, all of the substrates may, if desired, be converted to salts such as, for example, the hydrochloride, hydrobromide, acetate, or formate salts of the amino acids.

Each of the substrates, when exposed to its corresponding enzyme, is cleaved, the amino acid moiety being released or coupling with a suitable acceptor such as glycylglycine, to leave the fluorogenic primary amine (i.e., substrate (A), as identified above, in which the substituent for $R_3$ is a hydrogen atom). All of such fluorogenic aromatic amines have peak excitation and emission characteristics, when exposed to ultraviolet light, which are sufficiently close to those of an NADH-linked test ($\lambda ex=340$ nm; $\lambda em=465$ nm) to permit fluorometric activity measurements using the same equipment and filters employed for such standard NADH tests. Specifically, such chromophores have peak excitation characteristics at a wavelength within the range of 320 to 380 nm and peak emission characteristics at a wavelength within the range of 420 to 480 nm. For example, if substrate (A) has methoxy groups as $R_1$ and $R_2$, then the resulting chromophore will have a peak excitation wavelength of about 335 nm and a peak emission wavelength of about 445 nm.

In practicing the method of this invention, substrate is first dissolved in a sterile aqueous solution which preferably contains a suitable buffer to insure that the pH will be maintained at or near the optimum pH of the enzyme of interest. For example, where the enzyme to be measured is γ-glutamyl transpeptidase, the reaction may be measured over a broad range of pH values from about 7.5 to 9.0, a pH of 8.2 yielding maximum activity in the fluorometric assay system. The substrate solution is mixed with the sample (suspension or solution) and transferred to a suitable cuvet with any suitable fluorometer being used to measure front-surface fluorescence. The rate of production of the fluorogenic compound is directly proportional to the amount of transferase present in the sample.

The following examples are further illustrative of the invention:

EXAMPLE 1

Serum γ-glutamyl transpeptidase may be measured fluorometrically by utilizing γ-(L-glutamyl)-5-aminoisophthalic acid, dimethyl ester, hydrochloride salt, as the substrate. Such substrate has the structural formula:

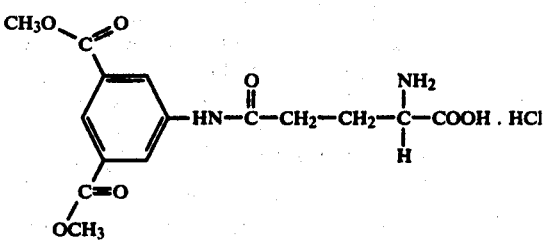

The reagent solution contained 5 mM substrate, 55 mM glycylglycine, and 100 mM Tris buffer (pH 8.2 at 25° C.), the solution volume being 1.5 ml. The reagent solution was warmed to 37° C., sample was added (volume at 0.05 ml), the reactants were mixed and pumped into a flow-through cuvet. The rate of increase in fluorescence was then measured for a minimum of 4 minutes using a front-surface instrument ($\lambda ex=365$ nm; $\lambda em=465$ nm). By such a procedure, the rate of change in fluorescence of the end product (5-aminoisophthalic acid, dimethyl ester) resulting from the hydrolysis of the substrate was measured, and the slope was calculated as the change in fluorescence per minute of reaction.

EXAMPLE 2

The results of serum samples tested in accordance with Example 1 were compared with the results of colorimetric assays run on the same patient samples, using GGTP reagent as marketed by Dade Division of American Hospital Supply Corporation and following the method set forth in the package instructions. To facilitate interpretation of data, the ΔF/min. was changed to International Units per liter (IU/L) by totaling IU/L and ΔF/min. and deriving a factor IU/ΔF. The sera was tested in two groups of 14, one group representing undiagnosed conditions and the other diagnosed conditions, and the following results were obtained:

| Sample | γ-Glutamyl Transpeptidase Activity (IU/L) | |
|---|---|---|
| | Fluorometric | Colorimetric |
| 1 | 47 | 45 |
| 2 | 52 | 51 |
| 3 | 12.5 | 17 |
| 4 | 85.4 | 79 |
| 5 | 113.4 | 110 |
| 6 | 196.9 | 195 |

-continued

| | γ-Glutamyl Transpeptidase Activity (IU/L) | |
|---|---|---|
| Sample | Fluorometric | Colorimetric |
| 7 | 14.5 | 17 |
| 8 | 14.5 | 18 |
| 9 | 345 | 344 |
| 10 | 43.4 | 48 |
| 11 | 48.8 | 72 |
| 12 | 236.4 | 225 |
| 13 | 212.3 | 198 |
| 14 | 259.6 | 260 |
| 15 | 80.9 | 87 |
| 16 Metastatic Cancer | 87.5 | 119 |
| 17 Gastritis | 89.5 | 94 |
| 18 Dehydration | 166.4 | 172 |
| 19 Obst. Jaundice | 23 | 26 |
| 20 Colostomy | 181 | 184 |
| 21 Hepatomegaly | 250.4 | 264 |
| 22 Cancer of Bladder | 146.7 | 148 |
| 23 Jaundiced | 164.0 | 167 |
| 24 Hip Problem | 215.4 | 200 |
| 25 Hodgkins | 14.7 | 14 |
| 26 Chest Pain, Hypertension | 62.8 | 47 |
| 27 Pulm. Embolus | 174.2 | 150 |
| 28 Sarcodosis | 193.5 | 178 |

The data demonstrate excellent correlation between the fluorometric method and the conventional colorimetric method for the determination of serum levels of γ-glutamyl transpeptidase.

EXAMPLE 3

The γ-(L-glutamyl)-5-aminoisophthalic acid, dimethyl ester, hydrochloride salt, used as the substrate in Example 1 may be prepared by mixing phthaloyl glutamic anhydride (13.2 g, 0.051 mole) and 5-aminoisophthalic acid, dimethyl ester (10.4 g, 0.050 mole) in 60 ml of dioxane, and stirring same at 55°–60° C. (bath temperature) for 1.5 hours. After evaporation of the solvent, the residue is then dissolved in 200 ml of methanol and hydrazine hydrate (7.5 g, 0.15 mole). The solution should then be filtered and allowed to stand at room temperature (2 days). A resulting white precipitate is then collected, washed with 100 ml of water and 25 ml of ethanol, agitated in 100 ml of 0.5 N hydrochloric acid, and filtered. The filtrate is treated with sodium bicarbonate to give a pH of 6.5 to 7.0, and the precipitate (8 g) is collected and dried. The hydrochloride salt may then be prepared by dissolving 1 gram of the glutamyl derivative in a solution of 0.3 ml of concentrated hydrochloric acid and 6 ml of methanol. After evaporation of the methanol, the solid is then dried under reduced pressure.

EXAMPLE 4

The following process may be used to prepare other 5-aminoisophthalic acid derivatives which may then be coupled to appropriate amino acid constituents as indicated.

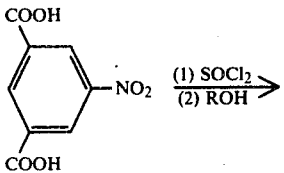

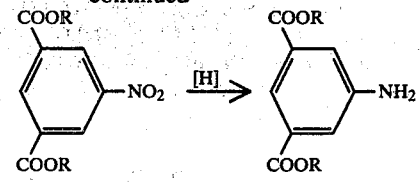

Where an amide is to be formed, $RNH_2$ is substituted for ROH in this equation. In either event, the end product is then reacted with the particular amino acid desired in the appropriate form (as illustrated in Example 3 in connection with phthaloyl glutamic anhydride) to produce the final amino acid derivative of aminophthalic acid to be used as a substrate for determining transpeptidase and/or protease activity.

While in the foregoing we have disclosed the invention in considerable detail for purposes of illustration, it will be understood by those skilled in the art that many of these details may be varied without departing from the spirit and scope of the invention.

We claim:

1. A reagent for use in a fluorometric determination of transferase and protease activity, said reagent comprises a substrate selected from the group consisting of

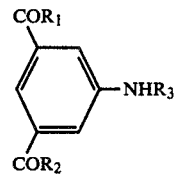

wherein each of $R_1$ and $R_2$ is —OH, —$NH_2$, $NHCH_3$, —$NHC_2H_5$, —$N(CH_3)_2$, —$N(C_2H_5)_2$, —$N((CH_3)(C_2H_5))$, —$OCH_3$, or $O(CH_2)_nCH_3$, n is an integer of 1 through 4, and wherein $R_3$ is an amino acid moiety capable of being cleaved from the remainder of said substrate in the presence of a transferase or protease having activity specific to that substrate and a buffer which maintains pH at or near the optimum pH of the transferase or protease.

2. The reagent of claim 1 wherein $R_3$ is an amino acid moiety transferable to glycylglycine when said substrate is reacted with glycylglycine in the presence of a transferase having activity specific to said substrate.

3. The reagent of claim 2 in which each of $R_1$ and $R_2$ is —$OCH_3$, said substrate being useful in the fluorometric determination of γ-glutamyl transpeptidase.

4. A reagent suitable for use in a fluorometric determination of transferase activity of γ-glutamyl transpeptidase comprising a γ-glutamyl derivative of dimethyl-5-amino isophalate, or salts thereof; an acceptor of the glutamyl moiety when said derivative is cleaved in the presence of γ-glutamyl transpeptidase; and a buffer for maintaining a pH within the range of 7.5 to 9.0.

5. The reagent of claim 4 in which said acceptor is glycylglycine.

6. A fluorometric method for determining the activity of transferases and proteases in samples of biological fluids, comprising the steps of mixing and reacting a substrate and a sample of body fluid containing a transferase or protease capable of cleaving said substrate; then exposing the mixture to ultraviolet light having a wavelength within the range of 320 to 380 nm; and measuring the rate of change in fluorescence at a wavelength within the range of 420 to 480 nm; said substrate being selected from the group consisting of

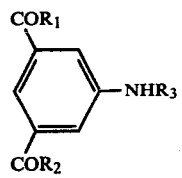

wherein each of $R_1$ and $R_2$ is —OH, —$NH_2$, $NHCH_3$, —$NHC_2H_5$, —$N(CH_3)_2$, —$N(C_2H_5)_2$, —$N(CH_3)(C_2H_5)$, —$OCH_3$, or $O(CH_2)_nCH_3$, n is an integer of 1 through 4, and wherein $R_3$ is an amino acid moiety capable of being cleaved from the remainder of said substrate in the presence of a transferase having activity specific to that substrate.

7. The method of claim 6 in which the reaction mixture is exposed to ultraviolet light having a wavelength of approximately 365 nm.

8. The method of claim 6 in which the change in fluorescence is measured at a wavelength of about 465 nm.

9. The method of claim 6 in which said mixing step includes mixing glycylglycine with said substrate and sample; $R_3$ being an amino acid moiety transferable to glycylglycine during said mixing step.

10. The method of claim 9 in which $R_3$ is γ-glutamyl and said transferase is γ-glutamyl transpeptidase.

11. A fluorometric method for determining the activity of γ-glutamyl transpeptidase in a sample of biological fluid, comprising the steps of mixing and reacting a γ-glutamyl derivative of 5-aminoisophthalic acid, dimethyl-5-aminoisophtholate, or salts thereof, with a γ-glutamyl acceptor, a buffer for maintaining a pH within the range of 7.5 to 9.0, and a sample of biological fluid containing γ-glutamyl transpeptidase; then exposing the mixture to ultraviolet light having a wavelength within the range of 320 to 380 nm; and measuring the rate of change in fluorescence at a wavelength within the range of 420 to 480 nm.

12. The method of claim 11 in which the reaction mixture is exposed to ultraviolet light having a wavelength of approximately 365 nm.

13. The method of claim 11 in which the change in fluorescence is measured at a wavelength of about 465 nm.

14. The method of claim 11 in which said acceptor is glycylglycine.

* * * * *

UNITED STATES PATENT AND TRADEMARK OFFICE
CERTIFICATE OF CORRECTION

PATENT NO. : 4,167,449

DATED : September 11, 1979

INVENTOR(S) : Robert J. Gargiulo and Richard C. Driscoll

It is certified that error appears in the above-identified patent and that said Letters Patent are hereby corrected as shown below:

Column 2, line 50 to end; column 3, lines 1-17, the prefix "(A)" should appear as a suffix for each item under the heading "Substrate" as follows:

```
Lys-ala-(A)
Z-ala-arg-arg-(A)
BZ-val-lys-lys-arg-(A)
CBZ-arg-arg-(A 2HCl)
N-CBZ-arg-arg-arg-(A diacetate)
L-arg-arg-(A 3HCl)
Z-gly-gly-arg-(A)
Pro-arg-(A)
α-BZ-phe-val-arg-(A)
L-cystine-(di-A)
γ-glutamyl-(A)
L-leu-gly-gly-(A formate)
Leu-(A)
BZ-arg-pro-gly-phe-phe-leu-(A)
Phe-pro-ala-met-(A)
Glutaryl-gly-L-phe-(A)
```

UNITED STATES PATENT AND TRADEMARK OFFICE
CERTIFICATE OF CORRECTION

PATENT NO. : 4,167,449
DATED : September 11, 1979
INVENTOR(S) : Robert J. Gargiulo and Richard C. Driscoll It is certified that error appears in the above–identified patent and that said Letters Patent are hereby corrected as shown below:

```
Gly-pro-(A)
CBZ-pro-ala-gly-pro-(A)
His-ser-(A)
N-CBZ-L-pro-L-phe-L-his-L-leu-L-leu-L-val-L-tyr-L-ser-(A)
N-CBZ-gly-L-met-(A)
Glutaryl-ala-ala-(A)
BZ-arg-pro-gly-phe-phe-pro-(A)
Ala-(A)
BZ-arg-(A)
BZ-arg-gly-leu-(A)
Met-(A)
BZ-arg-gly-tyr-(A)
Ser-tyr-(A)
```

Signed and Sealed this

Twenty-first Day of April 1981

[SEAL]

Attest:

*Attesting Officer*

RENE D. TEGTMEYER

*Acting Commissioner of Patents and Trademarks*